United States Patent [19]

Chabala et al.

[11] 4,199,569

[45] Apr. 22, 1980

[54] SELECTIVE HYDROGENATION PRODUCTS OF C-076 COMPOUNDS AND DERIVATIVES THEREOF

[75] Inventors: John C. Chabala, Westfield; Michael H. Fisher, Bridgewater, both of N.J.

[73] Assignee: Merck & Co., Inc., Rahway, N.J.

[21] Appl. No.: 928,111

[22] Filed: Jul. 31, 1978

Related U.S. Application Data

[63] Continuation-in-part of Ser. No. 838,603, Oct. 3, 1977, abandoned.

[51] Int. Cl.$^2$ .................... A61K 31/70; C07H 17/08
[52] U.S. Cl. .................................. 424/180; 536/9; 536/17 A; 260/343.41
[58] Field of Search ............... 536/9, 17; 260/343.41

[56] References Cited

U.S. PATENT DOCUMENTS

| | | | |
|---|---|---|---|
| 3,853,842 | 12/1974 | Kishi et al. | 536/9 |
| 3,950,360 | 4/1976 | Aoki et al. | 260/343.2 R |

OTHER PUBLICATIONS

Chem. Abstract Cit. 86 (1977), 42838k.
Mishima, H. et al., Tetrahedron Letters, 10, pp. 711–714 (1975).
Journal of Antibiotics, 29(g), 1976, pp. 76–34, 76–42, 76–14, 76–16.

*Primary Examiner*—Johnnie R. Brown
*Assistant Examiner*—Blondel Hazel
*Attorney, Agent, or Firm*—David L. Rose; Harry E. Westlake

[57] ABSTRACT

Derivatives of C-076 are described in which the C-076 molecule, as series of macrolides, has a specific unsaturation, at the 22,23-position, catalytically reduced. Further reaction of the reduced C-076 compounds are also possible. The compounds thus produced have profound anthelmintic, insecticidal, ectoparasiticidal and acaracidal activity. Compositions containing the described C-076 derivatives as the active ingredient thereof are also disclosed.

20 Claims, No Drawings

SELECTIVE HYDROGENATION PRODUCTS OF C-076 COMPOUNDS AND DERIVATIVES THEREOF

CROSS REFERENCE TO RELATED APPLICATIONS

This application is a continuation-in-part of our copending application Ser. No. 838,603, filed Oct. 3, 1977 now abandoned.

BACKGROUND OF THE INVENTION

The term C-076 is used to describe a series of compounds isolated from the fermentation broth of a C-076 producing strain of *Streptomyces avermitilis*. The morphological characteristics of the culture are completely described in copending U.S. application Ser. No. 772,601. The C-076 compounds are a series of macrolides, each of which is substituted thereon at the 13-position with a 4-(α-L-oleandrosyl)-α-L-oleandrose group. The 1-series of C-076 compounds also has a 22,23-double bond, as well as several other double bonds. The selective reduction of the 22,23-double bond, without affecting the remaining double bonds is the subject matter of the instant application. The C-076 compounds and the instant derivatives thereof have a very high degree of anthelmintic and antiparasitic activity.

SUMMARY OF THE INVENTION

The C-076 series of compounds have the following structure:

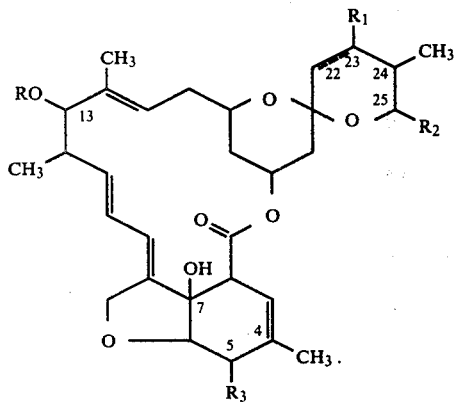

wherein R is the 4'-(α-L-oleandrosyl)-α-L-oleandrose group of the structure:

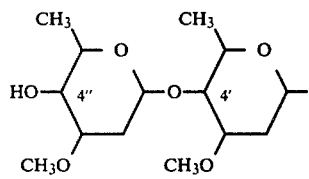

and wherein the broken line indicates a single or a double bond;
$R_1$ is hydroxy and is present only when said broken line indicates a single bond;
$R_2$ is iso-propyl or sec-butyl; and
$R_3$ is methoxy or hydroxy.

There are eight different C-076 compounds and they are given the designations A1a, A1b, A2a, A2b, B1a, B1b, B2a, B2b based upon the structure of the individual compounds.

In the foregoing structural formula, the individual C-076 compounds are as set forth below.

|     | $R_1$       | $R_2$     | $R_3$   |
| --- | ----------- | --------- | ------- |
| A1a | Double bond | sec-butyl | —$OCH_3$ |
| A1b | Double bond | iso-propyl | —$OCH_3$ |
| A2a | —OH         | sec-butyl | —$OCH_3$ |
| A2b | —OH         | iso-propyl | —$OCH_3$ |
| B1a | Double bond | sec-butyl | —OH     |
| B1b | Double bond | iso-propyl | —OH     |
| B2a | —OH         | sec-butyl | —OH     |
| B2b | —OH         | iso-propyl | —OH     |

The C-076 compounds with the 22,23-unsaturations are identified as the "1-series" and it is only these compounds which are reduced to prepare the instant derivatives. Either before or after the reduction of the 22,23-double bond further reactions may be carried out in which one or both of the α-L-oleandrose moieties are removed, or in which one or more of the available hydroxy groups are acylated.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of Merck & Co., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

The above microorganism is illustrative of a strain of *Streptomyces avermitilis* which can be employed in the production of the C-076 compounds. However, such description also embraces mutants of the above described microorganism. For example, those C-076 producing mutants which are obtained by natural selection or those producted by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

Thus, the compounds of the instant invention have the following structural formula:

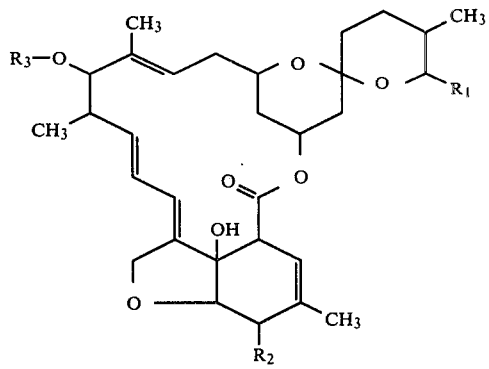

wherein

R$_1$ is iso-propyl or sec-butyl;

R$_2$ is methoxy, hydroxy or loweralkanoyloxy;

R$_3$ is hydrogen; loweralkanoyl; α-L-oleandrosyl; 4'-loweralkanoyl-α-L-oleandrosyl; 4'-(α-L-oleandrosyl)-α-L-oleandrosyl; 4''-loweralkanoyl-4'-(α-L-oleandrosyl)-α-L-oleandrosyl.

In the instant invention, the term "loweralkanoyl" is intended to include those alkanoyl groups of from 2 to 6 carbon atoms such as acetyl, propionyl, butyryl, pivaloyl and the like.

Preferred compounds of the instant invention are realized in the above structural formula when:

R$_1$ is iso-propyl or sec-butyl;

R$_2$ is methoxy or hydroxy; and

R$_3$ is hydrogen α-L-oleandrosyl or 4'-(α-L-oleandrosyl)-α-L-oleandrosyl.

Additional preferred compounds are realized when the "loweralkanoyl" group of R$_3$ is acetyl in the disaccharide, monosaccharide and aglycone compounds.

As is readily apparent from an analysis of the structure of the C-076 starting materials, there are five unsaturations in the 1-series of compounds. An object of the instant invention is to reduce the 22,23-double bond while not affecting the remaining four unsaturations or any other functional group present on the molecule. It is necessary to select a specific catalyst for the hydrogenation, one that will selectively hydrogenate the least hindered from among a series of unsaturations. The preferred catalyst for such a selective hydrogenation procedure is one having the formula:

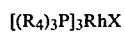

[(R$_4$)$_3$P]$_3$RhX wherein R$_4$ is loweralkyl, phenyl, or loweralkyl substituted phenyl and X is a halogen.

In the preferred catalyst R$_4$ is phenyl and X is chlorine, that is the compound tris(triphenylphosphine)-rhodium (I) chloride, which is also known as Wilkinson's homogeneous catalyst.

The reaction is carried out using a catalytic amount of the catalyst. The amount of catalyst is not critical and from 0.05 to 0.5 moles of the catalyst for each mole of starting material have been successfully employed. Molar ratios in the range of 0.25 to 0.40 are preferred.

The hydrogenation is carried out in a hydrogen atmosphere which may be either at atmospheric pressure or up to about 4 atmospheres pressure in a standard laboratory hydrogenation apparatus. A solvent is normally employed to dissolve both the starting materials and the catalyst. Preferred solvents are hydrocarbon solvents such as benzene, toluene, petroleum ether and other alkane hydrocarbons. The reaction is complete when the calculated amount of hydrogen has been taken up by the reaction. This will generally require from about 1 to 48 hours. The reaction may be carried out at from room temperature of about 75° C., however, room temperature is preferred. The hydrogenation products are isolated and purified by techniques known to those skilled in the art.

Other reactions may be carried out on the C-076 starting materials or on the hydrogenated products to prepare the compounds of this invention. While it is possible to complete all of the other reactions on the C-076 starting material and have the hydrogenation step as the final reaction, it is preferred to carry out the hydrogenation step first. Because the 22,23-double bond is somewhat susceptible to nucleophilic addition, reaction conditions for removing the sugar groups or acylating the hydroxy groups must be carefully controlled if the 22,23-double bond is present. If the 22,23-double bond is hydrogenated first, the subsequent sugar removal and acylation is rendered more facile.

Thus, the additional reactions which may be carried out to prepare the compounds of this invention are the selective removal of one or both of the α-L-oleandrosyl moieties or the selective acylation of the susceptible hydroxy groups.

The reaction conditions which are generally applicable to the preparation of both the monosaccharide and aglycone involve dissolving the C-076 compound or the hydrogenated C-076 compound in an aqueous acidic non-nucleophilic organic solvent, miscible with water, preferably dioxane, tetrohydrofuran, dimethoxyethane, dimethyl formamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°-40° C., preferably at room temperature, for from 6 to 24 hours. The lower concentrations of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the C-076 compounds or of the hydrogenated C-076 compounds utilizes a different solvent system for the monosaccharide and the aglycone. The procedure for the preparation of the monosaccharide uses 1% acid by volume in isopropanol at from 20°-40° C., preferably room temperature, for from 6 to 24 hours. For the preparation of the aglycone, 1% acid, by volume, in methanol under the foregoing reaction conditions has been found to be appropriate.

When this procedure is employed on the starting material (the compounds with the 22,23-double bond)

there is a possibility of nucleophilic addition to the double bond. If such occurs, chromatographic purification will remove the by-product in order to allow for further reactions.

The acids listed above are appropriate for this process, and again sulfuric acid is the preferred acid.

The above described compounds are isolated from the reaction mixture and mixtures of compounds are separated using techniques known to those skilled in this art, and in particular the chromatographic techniques described above.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures.

The acrylation reagents employed are generally the halide, preferably the chloride, of the above loweralkanoyl groups. That is the loweralkanoyl halide reagent is generally employed.

In addition, the acylation reagent could be in the form of the anhydride or of the halo formate. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethylamine and the like. The basic compound is required in equimolar amounts relative to the numbered moles of hydrogen halide being liberated, however excess amounts, even using the basic compound as a solvent, are not detrimental.

In the case of the A1 compounds of C-076, or of the hydrogenated C-076 A1 compounds there is only a single hydroxy group, 4" hydroxy, which may be acylated. The formation of the monosaccharide or the aglycone still leaves only a single hydroxy group which may be acylated, that is the 4' or 13 hydroxy group.

In the case of the 4", 4' and 13 hydroxy groups of C-076 A1 compounds, the acylating reagent is dissolved in a suitable solvent, pyridine is preferred, and the acylating reagent added. The reaction is maintained at from 0° C. to room temperature for from 4 to 24 hours. The product is isolated using known techniques.

The B1 compounds have 2 available hydroxy groups: at the 4"(4' or 13) and the 5-positions. However, the two hydroxy groups have similar reactivities. When the reaction of the acylating agent in pyridine is carried out at about room temperature for from 4 to 24 hours, the diacyl compound is recovered. When the reaction is carried out at 0° C. a mixture of the 4"(4' or 13) and 5 monoacyl compounds are recovered. To recover individual compounds, the mixture is placed on a chromatographic column or a preparative layer chromatographic plate of alumina or silica gel and the individual compounds are readily isolated. In addition, techniques such as high pressure liquid chromatography may be employed to separate mixtures of acylated compounds.

The acyl compounds thus prepared are isolated from the reaction mixture using techniques known to those skilled in this art.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The hydrogenated C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active monosaccharide or aglycone C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated C-076 compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 derivative employed, the compounds of this invention are usually fed at concentrations of between 0.00001 to 0.002% in the feed in order to achieve the desired antiparasitic result.

In using the compounds of this invention, the individual hydrogenated C-076 components may be prepared and used in that form. Alternatively, mixtures of two or more of the individual hydrogenated C-076 components may be used, as well as mixtures of the parent C-076 compounds other C-076 compound or other active compounds not related to C-076 and the compounds of this invention.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 75:25 to 99:1. The differences between the "a" series and "b" series is constant throughout the C-076 compounds and consists of a sec-butyl group and an iso-propyl group respectively at the 25 position. This difference, of course, does not interfere with any of the instant reactions. In particular may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% C-076 B1a or A1a and 20% C-076 B1b or A1b. Thus the preferred composition of this invention is one which contains about 80% of the "a" component and 20% of the "b" component.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The hydrogenated C-076 derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

22,23-Dihydro C-076 A1a 51.0 Mg of C-076 A1a and 14.4 mg. of tris (triphenylphosphine) rhodium (I) chloride are combined in 3.5 ml. of benzene and hydrogenated for 20 hours at room temperature under atmospheric pressure. The crude reaction mixture is chromatographed on a preparative layer chromatography plate eluting twice with 10% tetrahydrofuran in chloroform. The product is removed from the support using ethyl acetate which is evaporated to dryness and the residue analyzed with 300 MHz nuclear magnetic resonance and mass spectroscopy indicating the preparation of 22,23-dihydro C-076 A1a.

EXAMPLE 2

22,23-Dihydro C-076 B1a

The solution of 87.3 mg. of C-076 B1a in 6 ml. of benzene containing 25 mg. of tris (triphenylphosphine rhodium (I) chloride is hydrogenated for 4 hours at room temperature under 1 atmosphere of hydrogen pressure. Preparative layer chromatography on silica gel eluting with 20% tetrahydrofuran in chloroform recovers starting material. The sample is rehydrogenated following the above conditions for 19 hours. Preparative layer chromatography recovers 55 mg. of 22,23-dihydro C-076 B1a which is identified by mass spectrometry and 300 MHz nuclear magnetic resonance.

EXAMPLE 3

22,23-Dihydro C-076 B1a

A solution of 1.007 g. of C-076 B1a, 314 mg. of tris (triphenylphosphine) rhodium (I) chloride and 33 ml. of benzene is hydrogenated for 21 hours at room temperature under 1 atmosphere of hydrogen pressure. The solvent is removed in vacuo and the residue dissolved in a 1:1 mixture of methylene chloride and ethyl acetate and filtered. The filtrate is placed on a column of 60 g. of silica gel eluting with a 1:1 mixture of methylene chlorid and ethyl acetate taking 10 ml. fractions. Fractions 14–65 are combined and evaporated to dryness affording 1.118 g. of a solid material which is indicated by high pressure liquid chromatography to be a 60/40 mixture of the hydrogenated product and starting material. The mixture is rehydrogenated in 55 ml. of benzene adding 310 mg. of tris (triphenylphosphine) rhodium (I) chloride and stirring for 21 hours at room temperature under 1 atmosphere of hydrogen pressure. The solvent is removed in vacuo and the residue chromatographed on 80 g. of silica gel using 40:60 mixture of ethyl acetate and methylene chloride as eluant. 10 Ml. fractions are taken and the product appears in fractions 26–80. These fractions are combined and evaporated to dryness in vacuo affording a yellow oil. The oil is dissolved in benzene and lyophilized affording a pale yellow powder which is identified as 22,23-dihydro C-076 B1a by mass spectrometry and 300 MHz nuclear magnetic resonance. 0.976 G. of product is obtained.

EXAMPLE 4

22,23-Dihydro C-076 A1a Monosaccharide 11.2 Mg. of 22,23-dihydro C-076 A1a is dissolved in 1.1 ml. of 1% sulfuric acid in isopropanol and stirred for 20 hours at room temperature. The reaction mixture is diluted with chloroform to a volume of about 5.0 ml. and washed with saturated aqueous sodium bicarbonate solution and sodium chloride solution. The organic layer is dried over sodium sulfate and evaporated to dryness in vacuo affording an oil. The oil is placed on a silica gel preparative layer chromatography plate and eluted with 5% tetrahydrofuran in chloroform. The product is removed from the plate and lyophilized from benzene affording 5.2 mg. of a white powder which is identified by 300 MHz nuclear magnetic resonance and mass spectrometry as 22,23-dihydro C-076 A1a monosaccharide.

EXAMPLE 5

22,23-Dihydro C-076 A1a Aglycone 10.1 Mg. of 22,23-dihydro C-076 A1a is stirred for 20 hours in 1.1 ml. of 1% sulfuric acid in methanol at room temperature. The reaction mixture is treated as in Example 4 affording an oil which is purified by preparative layer chromatography on silica gel eluting with 5% tetrahydrofuran in chloroform. The product is removed from the chromatography plate and lyophilized from benzene affording 4.2 mg. of a white powder which 300 MHz nuclear magnetic resonance and mass spectrometry indicate to be 22,23-dihydro C-076 A1a aglycone.

EXAMPLE 6

22,23-Dihydro C-076 B1a Monosaccharide

395 Mg. of 22,23-dihydro C-076 B1a is added to a stirred solution of 50 ml. of 1% sulfuric acid in isopropanol and the solution is stirred for 14 hours at room temperature. The reaction mixture is treated as in Example 4 affording 0.404 g. of a foam after lyophilization from benzene. The foam is chromatographed on 6 preparative layer silica gel chromatography plates eluting twice with 4% tetrahydrofuran in chloroform. The monosaccharide with a Rf 0.15 is collected and washed from the silica gel with a total of 650 ml. of ethyl acetate. The combined washings are evaporated to dryness and the residue lyophilized from benzene to afford 0.2038 g. of 22,23-dihydro C-076 B1a monosaccharide which high pressure liquid chromatography indicates to be essentially pure.

EXAMPLE 7

22,23-Dihydro C-076 B1a Aglycone 9.7 Mg. of 22,23-dihydro C-076 B1a is stirred overnight in 1 ml. of a 1% sulfuric acid in methanol solution. The reaction mixture is treated as in Example 4 and the solid material treated with preparative layer chromatography on silica gel eluting with 10% tetrahydrofuran in chloroform. The oil recovered from the chromatography plate is lyophilized from benzene affording 4.7 mg. of a white powder which 300 MHz nuclear magnetic resonance and mass spectrometry indicate to be 22,23-dihydro C-076 B1a aglycone.

EXAMPLE 8

22,23-Dihydro C-076 B1a Aglycone 0.486 G. of 22,23-dihydro C-076 B1a is added to a stirred solution of 50 ml. of 1% sulfuric acid in methanol and the reaction mixture stirred for 13 hours at room temperature. The reaction mixture is diluted with 250 ml. of methylene chloride and washed with 50 ml. of saturated aqueous potassium bicarbonate and 50 ml. of water. The aqueous layer is washed twice with 20 ml. portions of methylene chloride and the combined organic phases are dried with saturated brine and sodium sulfate and evaporated to dryness in vacuo affording 0.480 g. of a pale yellow foam. The foam is dissolved in 4 ml. of methylene chloride and placed on 4 preparative layer chromatography silica gel plates and eluted 4 times with 4% tetrahydrofuran and chloroform. The product is recovered from the silica gel plates affording an oily residue which is lyophilized from benzene affording 255.8 mg. of a white solid. Traces of methyl oleandroside are indicated to be present in the solid material. The white solid is then lyophilized again from benzene and placed under high vacuum for 20 hours to remove the impurity affording 22,23-dihydro C-076 B1a aglycone.

EXAMPLE 9

4"-O-acetyl-22,23-Dihydro C-076 A1a 6.8 Mg. of 22,23-dihydro C-076 A1a is dissolved in 40 drops of anhydrous pyridine, chilled to 0° C. and treated with 20 drops of acetic anhydride. The reaction mixture is allowed to warm to room temperature and stirred overnight. The reaction mixture is diluted with 5 ml. of ether and 6 ml. of water and the layers separated. The aqueous phase is washed twice with ether and the organic layers combined and back washed 3 times with water. The ether layer is dried over magnesium sulfate and evaporated to dryness in vacuo affording an oil. The oil is chromatographed on silica gel preparative layer chromatography plates eluting with 5% tetrahydrofuran in chloroform. The product is recovered from the plates and lyophilized from benzene affording 6.1 mg. of 4"-O-acetyl-22,23-dihydro C-076 A1a as determined by mass spectrometry at 300 MHz nuclear magnetic resonance.

EXAMPLE 10

4"-O-acetyl-22,23-Dihydro C-076 B1a and 4",5-di-O-acetyl 22,23-Dihydro C-076 B1a 18.6 Mg. of 22,23-dihydro C-076 B1a is dissolved in 63 drops (about 1 ml.) of dry pyridine and treated with 9 drops of acetic anhydride at 0° C. The reaction is stirred under nitrogen for 6 hours at 0° C. The mixture is then quenched with 5 ml. of water and extracted 3 times with 3 ml. portions of ether. The combined ether extracts are then washed 3 times with 3 ml. portions of water and dried over magnesium sulfate and evaporated to dryness in vacuo. The oil is chromatographed on preparative layer silica gel chromatography plates eluting twice with 5% tetrahydrofuran in chloroform affording 5.8 mg. of 4"-O-acetyl-22,23-dihydro C-076 B1a and 5.8 mg of 4",5-di-O-acetyl-22,23-dihyro C-076 B1a after lyophilization from benzene. The structures are confirmed by 300 MHz nuclear magnetic resonance and mass spectrometry.

EXAMPLE 11

22,23-Dihydro C-076 B1a

39 G. of C-076 B1a is dissolved in 1540 ml. of toluene and introduced into a 4 liter stirred autoclave. To this is added 3.9 g. of tris (triphenylphosphine) rhodium (I) chloride (Wilkinson's catalyst). A hydrogenation pressure of 40 psi. and a temperature of 40° C. is maintained with stirring for 4½ hours. At the end of this period liquid chromatographic analysis indicates 98% yield of dihydro C-076 B1a with 1.5% of tetrahydro C-076 B1a. The toluene is removed by evaporation in vacuo and the dark red gum is dissolved in ethanol at a rate of 4 ml. of ethanol per gram of product. Formamide at a rate of 10 ml. per gram of product is added and the solution heated on the steam bath to 40°-50° while added water at a rate of 2 ml. per gram of product. After crystallization commences the heat is removed and the solution allowed to cool slowly with stirring overnight. The solid is filtered off and washed with a mixture 3 parts water and 1 part ethanol and dried in vacuo overnight. The solids are dissolved in 150 ml. of ethanol and warmed to 35°-40° C. on the steam bath. Water, 150 ml. is added slowly with stirring. When solution is complete at 35° C. the heat is removed and the solution allowed to cool slowly overnight. The crystals are removed by filtration and washed with 50% aqueous ethanol and dried in vacuo overnight affording 32.55 g. of 22,23-dihydro C-076 B1a with a m.p. of 155°-157° C.

PREPARATION 1

A 250 ml. baffled Erlenmeyer flask containing 50 ml. of the following medium:

| | |
|---|---|
| Lactose | 2.0% |
| Distiller's soluble | 1.5% |
| Autolyzed yeast, Ardamine pH | 0.5% |
| pH - before sterilization | 7.0 | is inoculated with the contents of one frozen vial of *Streptomyces avermitilis* MA 4848 and incubated on a rotary shaker at 28° C. for 24 hours at 150 RPM.

10 Ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:

| | |
|---|---|
| Lactose | 2.0% |
| Distiller's solubles | 1.5% |
| Autolyzed yeast, Ardamine pH | 0.5% |
| Polyglycol 2000 | 0.32 ml./liter |

| | |
|---|---|
| pH - before sterilization | 7.0 |

The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:

| | |
|---|---|
| Dextrose | 4.5% |
| Peptonized milk | 2.4% |
| Autolyzed yeast, Ardamine pH | 0.25% |
| Polyglycol 2000 | 2.5 ml./liter |
| pH - before sterilization | 7.0 |

The fermentation continues for 144 hours at 26° C. with an air flow rate of 54.3 cubic feet per minute and agitation of 120 RPM.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

PREPARATION 2

The 60 liter solution of C-076 in methylene chloride of the previous example is concentrated to dryness in vacuo and the residue is combined 3 times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2 layer solution is agitated for 5 minutes and the lower layer (ethylene glycol and methanol) is separated. The heptane solution is washed with a mixture of 20 liters of ethylene glycol and 6.3 liters methanol. After five minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a minimum volume, keeping the temperature less than 25° C. 40 Liters of methylene chloride is added to the residue and the solution is evaporated to dryness. This procedure is repeated and the final residue concentrated in vacuo at 50° C. to dryness.

PREPARATION 3

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. these fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

PREPARATION 4

A 30 centimeter diameter column is prepared in methanol with 36 kilograms of Sephadex LH-20 (available from Pharmacia Fine Chemicals, 800 Centennial Avenue, Piscataway, N.J. 08854) and washed with a solvent consisting of 10 parts methylene chloride, 10 parts hexane and one part methanol. One-fourth of the C-076 solution of Example 10 is applied to the column and the column eluted at a rate of 250 ml. per minute. Two 20 liter forecuts are collected and discarded followed by 20 two liter rich cuts (identified as fractions 1-20), followed by a single 20 liter tail cut, which is discarded. Fractions 1-8 are found to contain the C-076 A compounds and fractions 9-20 are found to contain the C-076 B compounds.

PREPARATION 5

The process of Preparation 4 is repeated on the same scale three more times and all of the fractions containing the C-076 B components (fractions 9-20) are combined and evaporated to dryness, affording 818 g. of crude mixed C-076 B components. The sample is found to contain 55% C-076 B1 and 39% of C-076 B2. 680.5 G. of this sample is dissolved in 2 liters of methylene chloride and placed in a 22 liter three neck round bottom flask followed by the addition of 13.6 liters of methanol. The methylene chloride is removed by distillation. 13.6 Liters of ethylene glycol is added as the methanol is being distilled under reduced pressure. The rate of distillation is maintained such that the temperature of the solution did not go below 65° C. When the addition of the ethylene glycol is complete, the solution is allowed to cool at 5° C. for sixteen hours. The crystals are filtered and washed with 1 liter of cold ethylene glycol. The crystals are then redissolved in 2 liters of methylene chloride the solution placed in a 22 liter three necked round bottom flask. The procedure described above is repeated twice. The first time 12.5 liters each of methanol and ethylene glycol is employed and the second time 13.6 liters each of methanol and ethylene glycol is employed. The final crystals are washed with 1 liter of cold ethylene glycol and 1 liter of water. The crystals are dissolved in 4 liters of water and dried by filtering through sodium sulfate. The benzene solution is concentrated to a volume of 2 liters and lyophilized affording 241.2 gm. of a white powder consisting of 98% C-076 $B_1$ and 1% of C-076 $B_2$.

The mother liquors (22 liters) from the first two crystallizations above are combined and diluted with 22 liters of water. The aqueous solution is extracted with 60 liters of toluene and again with 15 liters of toluene. The toluene extract is then washed with 48 liters of water. The organic phase is filtered through Super-Cel to remove any residual water and evaporated affording 336 gm. of solid material consisting of 79% C-076 $B_2$ and 16% C-076 $B_1$ compounds.

PREPARATION 6

In the four Sephadex LH-20 columns of the procedure of Preparation 4, fractions 1–8 contain the C-076 A compounds and are combined. By HPLC analysis the mixture is found to contain 252 g. of C-076 A2a, 16 g. of A2b, 94 g. of A1a and 24 g. of A1b. The material is dissolved in a solvent system consisting of hexane:-toluene:methanol in the proportion of 6:1:1 and applied to the Sephadex LH-20 column of the same dimensions as the one used in Preparation 4 in the above solvent. Fractions are collected at the rate of 250 ml. per minute and a 20 liter forecut is collected and discarded. Further elution affords 2 additional 20 liter forecuts which are also discarded and 50 four liter rich cuts which contain C-076 A compounds. Fractions 3–8 are found to contain predominately C-076 A1 components (40.2 g. A1a and 6.7 g. A1b), and fractions 29–36 are found to contain C-076 A2 compounds (117.2 g. A2a and 7.35 g. of A2b). Fractions 9–28 contain a mixture of C-076 A1 and A2 compounds.

PREPARATION 7

A sample of 150 g. of C-076 B1 from Preparation 5 is dissolved in 3 liters of a solvent mixture of hexane:-toluene:methanol in the ratio of 3:1:1. The solution is passed through a column of Sephadex LH-20 (of the same dimensions as the one used in Preparation 4) in the above solvent taking fractions at the rate of 250 ml. per minutes. After two 20 liter portions of the solvent mixture are collected and discarded, forecut of 10 liters is taken and discarded. Then 30 richcuts of 2 liters each are taken. Fractions 1–13 and 25–30 are discarded. Fractions 14–16 are combined and contain 80 g. of predominately C-076 B1a. Fractions 22–24 are combined and contain 6.7 g. of predominately C-076 B1b. Fractions 17–21 contain a mixture of C-076 B1a and B1b.

Fractions 17–21 above are combined and concentrated and passed through a Sephadex LH-20 column with the same solvent system as above. Three 20 liter forecuts are taken and discarded. Richcuts are then taken as follows: 5 cuts of 2 liters each (fractions 1–5); 20 cuts of 1 liter each (fractions 6–25); and 10 cuts of 2 liters each (fractions 26–35). Fractions 1–15 are discarded; fractions 16–21 contain 13.5 g. of C-076 B1a and 0.4 g. of C-076 B1b; fractions 22–26 contain 44 g. of C-076 B1a and 0.13 g. of C-076 B1b; fractions 27–30 contain 10.2 g. of C-076 B1a and 0.8 g. of C-076 B1b.

PREPARATION 8

A mixture of all 8 C-076 components are chromatographed on a high pressure liquid chromatography column 4 mm.×30 cm. packed with 10 micron $\mu$ Bondapak $C_{18}$ silica gel (available from Waters Associates inc., Maple Street, Milford, Massachusetts 01757) eluting with 85:15 (v/v) methanol:water at a constant 40° C. At a flow rate of 1.2 ml. per minute all eight compounds are separated and the elution volumes, which under the foregoing constant conditions are characteristic of the individual compounds are as follows:

|  | Elution Volume (Ve) Ml |
| --- | --- |
| C-076 $B_2b$ | 5.90 |
| C-076 $B_2a$ | 6.52 |
| C-076 $A_2b$ | 7.12 |
| C-076 $A_2a$ | 7.88 |
| C-076 $B_1b$ | 8.36 |
| C-076 $B_1a$ | 9.60 |
| C-076 $A_1b$ | 10.24 |
| C-076 $A_1a$ | 11.88 |

The separation of C-076 "b" components from the respective "a" components is accomplished using techniques such as high pressure liquid chromatography. An absolute methanol solution of 30 microliters of a mixture of C-076 A1a and A1b, estimated to contain 30 micrograms of C-076 A1b is placed on a 3×250 mm. high pressure liquid chromatography column containing Spherisorb 5 micron ODS (available from Spectra Physics) as packing. The column is eluted with 85:15 methanol-water at a rate of 0.15 ml./min. The elution of the products are followed by observing the ultraviolet absorption of the eluent and collecting the individual components at the outlet of the UV monitor. 30 Micrograms of C-076 A1b is recovered in this manner.

What is claimed is:

1. A compound having the formula:

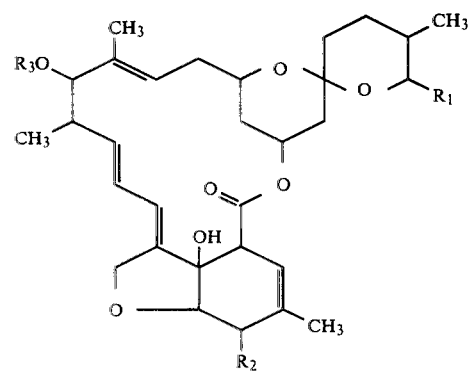

wherein
$R_1$ is iso-propyl or sec-butyl;
$R_2$ is methoxy, hydroxy or loweralkanoyloxy; and
$R_3$ is hydrogen; loweralkanoyl; α-L-oleandrosyl; 4'-loweralkanoyl-α-L-oleandrosyl; 4'-(α-L-oleandrosyl)-α-L-oleandrosyl, 4''-loweralkanoyl-4'-(α-L-oleandrosyl)-α-L-oleandrosyl.

2. The compound of claim 1 wherein:
$R_1$ is iso-propyl or sec-butyl;
$R_2$ is methoxy or hydroxy; and
$R_3$ is hydrogen, α-L-oleandrosyl or 4'-(α-L-oleandrosyl)-α-L-oleandrosyl.

3. The compound of claim 2 wherein $R_1$ is iso-propyl.

4. The compound of claim 2 wherein $R_1$ is sec-butyl.

5. The compound of claim 4 which is 22,23-dihydro-C-076 A1a.

6. The compound of claim 4 which is 22,23-dihydro-C-076 B1a.

7. The compound of claim 4 which is 22,23-dihydro-C-076 A1a aglycone.

8. The compound of claim 4 which is 22,23-dihydro-C-076 B1a aglycone.

9. The compound of claim 4 which is 22,23-dihydro C-076 A1a monosaccharide.

10. The compound of claim 4 which is 22,23-dihydro C-076 B1a monosaccharide.

11. The compound of claim 1 wherein the loweralkanoyl group of $R_3$ is acetyl.

12. The compound of claim 11 which is 4''-O-acetyl-22,23-dihydro C-076 A1a.

13. The compound of claim 11 which is 4''-O-acetyl-22,23-dihydro C-076 B1a.

14. The compound of claim 11 which is 4'', 5-di-O-acetyl 22,23-dihydro C-076 B1a.

15. A method for treating for parasites which comprises treating the animal or area infected with parasites with an effective amount of one or more compounds of claim 1.

16. The method of claim 15 wherein the active compound is C-076 B1a.

17. The method of claim 15 wherein the active compound is a mixture of about 80% C-076 B1a and 20% C-076 B1b.

18. A composition for the treatment of parasitic infections which comprises an inert carrier and one or more compounds of claim 1.

19. The composition of claim 18 wherein the active compound is C-076 B1a.

20. The composition of claim 18 wherein the active compound is a mixture of about 80% C-076 B1a and 20% C-076 B1b.

* * * * *